United States Patent [19]

Tanihara

[11] 4,388,474

[45] Jun. 14, 1983

[54] METHOD FOR THE PREPARATION OF GUANIDINE SULFAMATE

[75] Inventor: Koichi Tanihara, Ogoori, Japan

[73] Assignee: Director-General of the Agency of Industrial Science and Technology, Tokyo, Japan

[21] Appl. No.: 241,236

[22] Filed: Mar. 6, 1981

[30] Foreign Application Priority Data

Mar. 6, 1980 [JP] Japan ................................. 55-29363

[51] Int. Cl.$^3$ ........................................ C07C 143/837
[52] U.S. Cl. ................................................ 564/241
[58] Field of Search ......................................... 564/241

[56] References Cited

U.S. PATENT DOCUMENTS 2,567,676  9/1951  Marsh .................................. 564/241
2,567,677  9/1951  Marsh .................................. 564/241

FOREIGN PATENT DOCUMENTS 50-96527  7/1975  Japan ................................... 564/241
653522   11/1947  United Kingdom ................. 564/241
721620    1/1955  United Kingdom ................. 564/241

OTHER PUBLICATIONS

Sisler, H. et al., J. Am. Chem. Society, vol. 60, (1938), pp. 1947-1948.
Doyle, George J. et al., J. Am. Chem. Society, vol. 71, (1949), pp. 3491-3498.

Primary Examiner—Glennon H. Hollrah
Assistant Examiner—L. Hendriksen
Attorney, Agent, or Firm—Brisebois & Kruger

[57] ABSTRACT

The invention provides a novel method for the preparation of guanidine sulfamate from the reaction mixture of urea and an ammonium aqua-ammonosulfate, e.g. ammonium imidosulfonate, obtained by the reaction under atmospheric pressure followed by hydrolysis with water. Different from conventional procedures, the hydrolysis in the inventive method is carried out at a temperature not exceeding 100° C. or, preferably, at about 70° C., in which the retardation of the reaction velocity at the lower temperature is compensated for by admixing the aqueous solution of the reaction mixture with a portion of the hydrolysis product obtained in the preceding run. After completion of the hydrolysis reaction, the hydrolysis product is admixed with calcium hydroxide or oxide and the desired guanidine sulfamate is obtained from the liquid portion from which the excess of the calcium ions has been removed.

3 Claims, 3 Drawing Figures

METHOD FOR THE PREPARATION OF GUANIDINE SULFAMATE

BACKGROUND OF THE INVENTION

The present invention relates to a method for the preparation of guanidine sulfamate or, more particularly, to a method for the preparation of guanidine sulfamate by the reaction of an ammonium aqua-ammonosulfate and urea.

It is known that the reaction of urea and an ammonium aqua-ammonosulfate such as ammonium sulfamate, ammonium imidosulfonate, ammonium nitridosulfate and the like gives a reaction mixture mainly composed of guanidinium ions, ammonium ions, sulfamate ions, imidosulfonate ions and sulfate ions. This reaction may be carried out either in air or in an atmosphere of ammonia and also under atmospheric pressure or under a pressurized condition. The reaction mixture obtained by the reaction under atmospheric pressure is characterized by the higher content of the imidosulfonate ions than the reaction mixture obtained by the reaction under pressurization with ammonia.

It is an industrially feasible process to obtain guanidine salts such as guanidine sulfate and guanidine sulfamate useful, for example, as a flame retardant from the above reaction mixture by undertaking a suitable means for separation. Unfortunately, the separation of the guanidine salts from the reaction mixture is not a simple matter because so many kinds of ionic species are coexistent in the reaction mixture and most of the coexistent salts have a very large solubility in water. For example, no satisfactory results are obtained by a conventional physical or physicochemical method for separation such as precipitation of the salts by chilling or evaporating the solution or by the addition of a water-miscible organic solvent to the aqueous solution to decrease the solubility of the salt and a method by use of an ion-exchange resin. Accordingly, several methods for the separation have been proposed including a chemical process but none of them is satisfactory with its own problems from the standpoint of practicability.

For example, the inventor has previously disclosed a method for the separation of the guanidine salts in which the reaction mixture of urea and an ammonium aqua-ammonosulfate is treated with calcium carbonate to separate the desired guanidine sulfamate (see Japanese Patent Publication 50-21452). This method is, however, very time-consuming taking an extremely prolonged reaction time for completing the reaction with calcium carbonate by boiling an aqueous solution of the reaction mixture. Therefore, this method is economically disadvantageous, especially, when the cost for heating energy is large. In addition, this method of treatment with calcium carbonate is not applicable to the reaction mixture obtained by the reaction under atmospheric pressure with ammonium imidosulfonate or ammonium nitridosulfate as the ammonium aqua-ammonosulfate because of the presence of ammonium imidosulfonate in the reaction mixture.

With an object to overcome the above described difficulties, the inventor has further proposed an improved method (see Japanese Patent Disclosure 50-96527) for separating guanidine sulfate from the reaction mixture in which the reaction mixture obtained by the reaction under atmospheric pressure is heated in water at a temperature of 100° C. or higher to be converted into a mixture composed of guanidinium ions, ammonium ions, hydrogen ions and sulfate ions which is then treated with calcium oxide or calcium hydroxide. This method, however, must be carried out under a pressurized condition giving a great limitation to the practical application of the method.

SUMMARY OF THE INVENTION

It is therefore an object of the present invention to provide a novel and economical method for the preparation of guanidine sulfamate starting with the reaction of urea and an ammonium aqua-ammonosulfate under atmospheric pressure to give a reaction mixture which is then subjected to a process for the separation of the desired guanidine salt.

The process for the separation of the guanidine salt in the inventive method as described hereunder is based on the known fact that the imidosulfonate ions contained in the reaction mixture of urea and an ammonium aqua-ammonosulfate is readily hydrolyzed into hydrogen ions, sulfamate ions and sulfate ions by heating in an acidic condition with sulfuric acid even at a temperature below 100° C. and also on the novel discovery that the desired guanidine sulfamate is readily recovered from an aqueous solution containing guanidinium ions, ammonium ions, hydrogen ions, sulfamate ions and sulfate ions by the treatment with calcium hydroxide or oxide when the molar contents of the guanidinium ions and the sulfamate ions are approximately equal. The above mentioned hydrolysis of the imidosulfonate ions is described in Journal of the American Chemical Society, volume 71, page 3491 and expressed by the following reaction equation (I).

$$NH(SO_3)_2{}^{2-} + H_2O \rightarrow H^+ + SO_4{}^{2-} + H_2NSO_3{}^- \qquad (I)$$

Thus, the method of the invention for the preparation of guanidine sulfamate comprises the steps of (a) reacting urea and an ammonium aqua-ammonosulfate under atmospheric pressure to give a reaction mixture, (b) heating the reaction mixture dissolved in water at a temperature not exceeding 100° C. or, preferably, in the range from 65° C. to 85° C. to give a hydrolysis product mainly composed of guanidinium ions, ammonium ions, hydrogen ions, sulfamate ions and sulfate ions, of which the molar contents of the guanidinium ions and the sulfamate ions are substantially equal, (c) admixing the hydrolysis product with calcium hydroxide or calcium oxide, and (d) subjecting the hydrolysis product admixed with calcium hydroxide or calcium oxide to solid-liquid separation to give a liquid portion.

The liquid portion thus obtained contains mainly guanidinium ions, sulfamate ions and ammonia with greatly reduced contents of sulfate ions and calcium ions so that the desired guanidine sulfamate can be obtained therefrom by any conventional method such as evaporation to dryness followed, if desired, by recrystallization.

In the above described steps of the inventive method, it has been unexpectedly discovered that the reaction of the hydrolysis in the step (b) is greatly accelerated when the reaction mixture to be hydrolyzed as dissolved in water is admixed with a portion of the hydrolysis product obtained in the preceding run of the hydrolysis reaction to constitute a recycling process in which the portion of the hydrolysis product to be recycled to the succeeding run of the hydrolysis is preferably at least one fourth of the amount of the reaction mixture dissolved in water in the succeeding run.

DETAILED DESCRIPTION OF THE PREFERRED EMBODIMENTS

Figure 1:
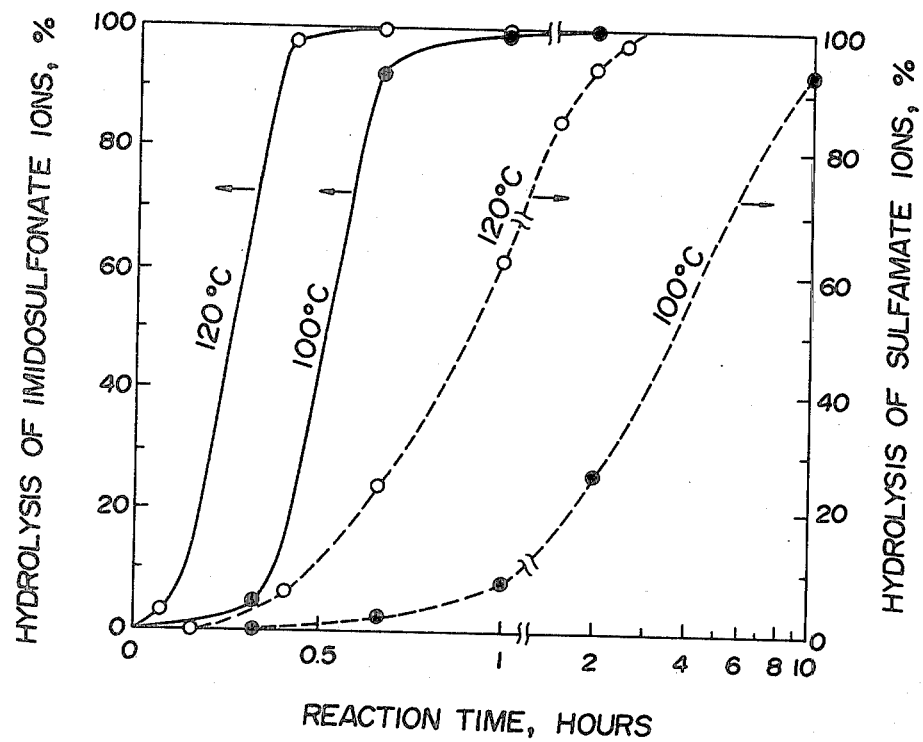
FIG. 1 illustrates the velocity of hydrolysis reaction of imidosulfonate ions and sulfamate ions at 100° C. and 120° C.

The starting materials in the inventive method are urea and an ammonium aqua-ammonosulfate. The ammonium aqua-ammonosulfate is a well known substance and obtained, for example, by the reaction of ammonia and sulfuric acid anhydride in the gaseous phase as a mixture of two kinds or more including ammonium sulfamate, ammonium imidosulfonate and ammonium nitridosulfate. Such a mixture of the ammonium salts may be used as such.

The reaction of urea and the ammonium aqua-ammonosulfate is carried out by blending these solid reactants and heating the blend in air or in an atmosphere of ammonia under atmospheric pressure. The reaction per se is well known in the art (see, for example, copending Japanese Patent Application 55-29362) but it should be noted in the inventive method that the blending ratio of the urea and the ammonium aqua-ammonosulfate must be carefully determined in order that desirably the molar contents of guanidinium ions and sulfamate ions in the hydrolysis product is approximately equal although a slight deviation from the above mentioned equimolar contents can be remedied after or before the hydrolysis reaction.

The next step is the hydrolysis of the above obtained reaction mixture with water. This hydrolysis reaction is preferably carried out at a temperature not exceeding 100° C. from the standpoint to avoid the troublesome operation under a superatmospheric pressure and to decrease the decomposition of the sulfamate ions. The above mentioned decreased decomposition of the sulfamate ions is well demonstrated by the experimental results shown in FIG. 1 obtained by heating a mixture of 13.8% of water and 86.2% of a typical reaction mixture composed of 14.4% of guanidinium ions, 15.1% of ammonium ions, 15.1% of sulfamate ions, 30.5% of sulfate ions and 24.9% of imidosulfonate ions, all % being given by % by weight, at 100° C. and 120° C. in a Teflon-lined pressure resistant reaction vessel and examining the percentages of the hydrolyzed amounts of the imidosulfonate ions and sulfamate ions. As is clear from the results, loss of the sulfamate ions by hydrolysis is greatly accelerated at a temperature of 120° C. in comparison with the reaction at 100° C. so that the selective hydrolysis of the imidosulfonate ions alone can hardly be achieved at 120° C. with suppression of the hydrolysis of the sulfamate ions even with an utmost care for the selection of the other reaction conditions.

Accordingly, it is a desirable condition that the temperature of the reaction mixture under hydrolysis with water is kept at a temperature not exceeding 100° C. However, the reaction velocity of the hydrolysis reaction of the imidosulfonate ions is very low when the reaction mixture is heated as an aqueous solution as such at a temperature not exceeding 100° C. taking unduly long time for the completion of the reaction. This is presumably because of the phenomenon of the formation of $HSO_4^-$ ions in the presence of a large amount of sulfate ions to decrease the concentration of hydrogen ions and consequently to retard the hydrolysis of the imidosulfonate ions as is discussed in Journal of the American Chemical Society, volume 71, page 3491.

A method for accelerating the hydrolysis is the addition of sulfuric acid to the reaction mixture under hydrolysis utilizing the benefit that sulfuric acid can readily be removed in the subsequent step of purification.

As an alternative method, the inventor unexpectedly discovered, taking into consideration the fact that hydrogen ions are produced by the hydrolysis of the imidosulfonate ions, that the reaction of hydrolysis can be greatly accelerated without the addition of sulfuric acid when a portion of the hydrolysis product obtained in the preceding run of the same hydrolysis reaction is recycled and added to the reaction mixture dissolved in water so that the reaction can be completed by heating within a remarkably shortened period of time.

Figure 2:
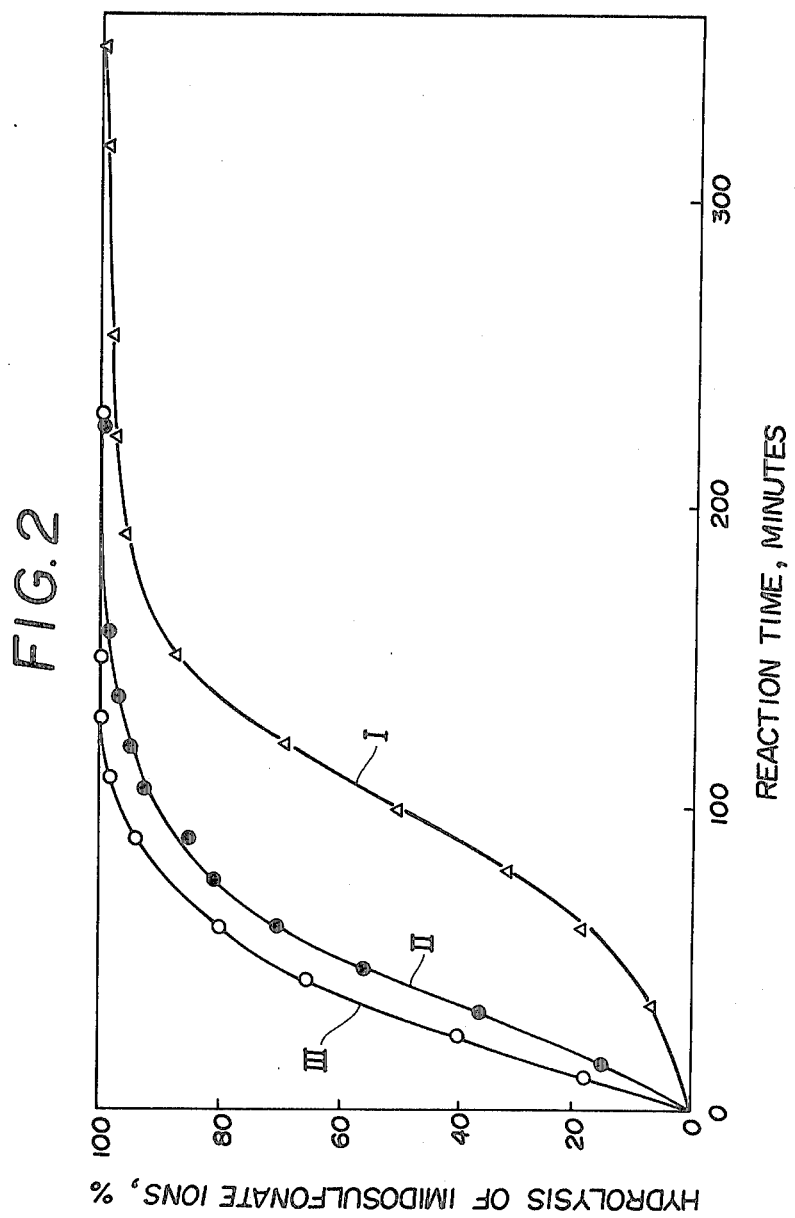
FIG. 2 illustrates the velocity of hydrolysis of imidosulfonate ions with different recycling ratios of the hydrolysis product from the previous run.

With an object to determine the optimum recycling ratio of the hydrolysis product, several simulating runs of the hydrolysis reaction were carried out with the reaction mixture as used in the experiments shown in FIG. 1 with varied recycling ratios. The reaction was undertaken by heating the reaction mixture dissolved in water in a solid content of 65% by weight of 70° C. with or without recycling of a portion of the hydrolysis product obtained in the previous run. FIG. 2 illustrates the results of the hydrolysis runs in which curve I is for the reaction without recycling and curves II and III are each for the hydrolysis reaction with the recycling ratio of ⅓ or 1/1, respectively. That is, one fourth of the hydrolysis product coming from the preceding run was recycled and three fourths were processed in the subsequent step in the experiment indicated by curve II while each a half amount of the preceding hydrolysis product was used for recycling and for processing in the subsequent step in the experiment indicated by curve III. It has been concluded from these results that the optimum recycling ratio is in the range from ⅓ to 1/1 in the hydrolysis reaction carried out at 70° C. with respect to the time taken for the reaction, throughput within a time, decrease in the hydrolysis of the sulfamate ions and workability, assuming that each of the runs is undertaken with the same amounts of the reactants as in the preceeding or succeeding run. In these experiments, the hydrolysis of the sulfamate ions was 1.38% with no recycling of the hydrolysis product after 350 minutes of the reaction and 1.07% with a recycling ratio of 1/1 after 231 minutes of the reaction.

Figure 3:
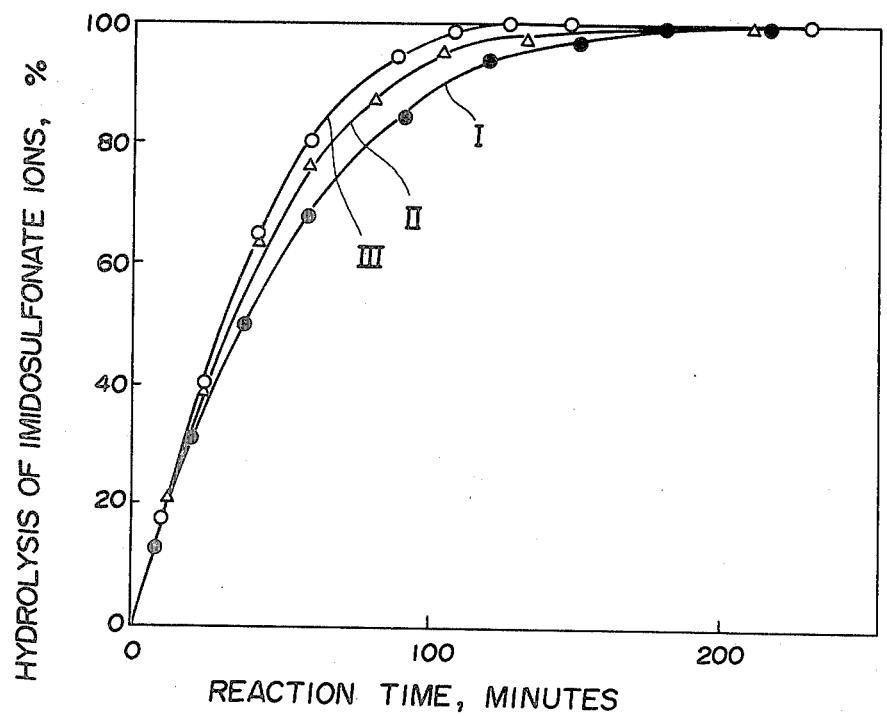
FIG. 3 illustrates the influence of the concentration of the reaction mixture on the velocity of the hydrolysis reaction.

Further, test runs of the hydrolysis of the imidosulfamate ions were undertaken with varied weight ratios of the reaction mixture and water but with the reaction temperature kept at 70° C. and the recycling ratio kept at 1/1 in all of the runs. FIG. 3 illustrates the results in which the concentration of the reaction mixture in the blend under hydrolysis was 30%, 50% or 65% by weight for curves I, II and III, respectively. The conclusion derived from the results is that the concentration is relatively ineffective on the rate of hydrolysis with the concentration in this range so that the concentration is no longer a restricting factor for the productivity.

When ammonium nitridosulfate is used as the ammonium aqua-ammonosulfate to be reacted with urea under atmospheric pressure, the resultant reaction mixture may sometimes contain a considerable amount of the unreacted ammonium nitrodosulfate, which causes, however, no particular troubles because it is very rapidly hydrolyzed into ammonium imidosulfonate and sulfuric acid according to the following reaction equation (II) as is taught in Journal of the American Chemical Society, volume 60, page 1947.

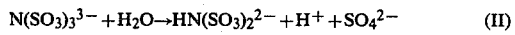

$$N(SO_3)_3{}^{3-} + H_2O \rightarrow HN(SO_3)_2{}^{2-} + H^+ + SO_4{}^{2-} \qquad (II)$$

The reaction mixture of urea and the ammonium aqua-ammonosulfate obtained under atmospheric pressure is now converted by the hydrolysis reaction of the imidosulfonate ions into a mixture composed mainly of guanidinium ions, ammonium ions, hydrogen ions, sulfamate ions and sulfate ions. The molar ratio of the guanidinium ions and the sulfamate ions in this hydrolysis product is desirably as close as possible to 1 although a small deviation from the desired condition of equal molar contents can be remedied subsequently without causing any particular problems in the following purification step. Of course, it is the most desirable that the above condition of the equimolar concentrations of the guanidinium ions and sulfamate ions is satisfied approximately in the product as hydrolyzed. Such a condition is spontaneously achieved when the reaction mixture of urea and the ammonium aqua-ammonosulfate has been prepared under optimum reaction conditions relative to the molar ratio of the reactants, reaction temperature and the like parameters so that no particular means for the adjustment of the concentration ratio is necessary in most cases at least in so far as the final desired product is crude quanidine sulfate.

When the molar concentration of the guanidinium ions is in excess over the sulfamate ions, a recommended method for the adjustment of the molar ratio is that the hydrolysis product is admixed with sulfamic acid or ammonium sulfamate in an amount equivalent to the excess amount of the guanidinium ions or, alternatively, the blend of the reaction mixture and water before hydrolysis is admixed with ammonium sulfamate, ammonium imidosulfonate, ammonium nitridosulfate or a mixture thereof in such an amount that the molar concentrations of the guanidinium ions and the sulfamate ions be equalized in the hydrolysis product.

When the molar concentration of the sulfamate ions is in excess over the guanidinium ions, on the other hand, the hydrolysis product may be admixed with guanidine sulfate in an amount to balance the excess of the sulfamate ions or, alternatively, admixed with ammonium nitrite in an amount equivalent to the excess of the sulfamate ions to be consumed by the reaction expressed by the following equation (III).

$$NH_2SO_3{}^- + NH_4NO_2 \rightarrow N_2 + NH_4{}^+ + SO_4{}^{2-} + H_2O \qquad (III)$$

The next step is the treatment of the hydrolysis product which calcium hydroxide or calcium oxide. Thus, the hydrolysis product obtained in the step (b) above is admixed with calcium hydroxide or calcium oxide in an amount at least equivalent or, preferably, in an amount of 1.2 to 1.5 times of the equivalent amount to the sulfuric acid and ammonium sulfate contained in the hydrolysis product. The reaction is carried out usually at room temperature with continuous agitation. When the reaction temperature is increased, the reaction is accelerated and a possibility is obtained to reduce the amount of the calcium hydroxide or calcium oxide to be added to the hydrolysis product. The reaction temperature, however, should not exceed 70° C. because decomposition of the quanidinium ions is increased at higher temperatures.

The principal components in the liquid portion obtained by solid-liquid separation of the hydrolysis product after the treatment which calcium hydroxide or oxide are guanidinium ions, sulfamate ions and ammonia accompanied by small amounts of calcium ions and sulfate ions. No particular difficulties are involved in the solid-liquid separation of the hydrolysis product containing calcium hydroxide or oxide by a conventional method such as filtration.

It is a relatively easy matter to recover the desired guanidinium sulfate from the thus obtained liquid portion or the filtrate solution by a suitable physicochemical method. For example, though not limited thereto, carbon dioxide gas is bubbled into the solution approximately to neutral to precipitate the calcium ions as calcium carbonate, which is removed by filtration, and the clear filtrate is evaporated to dryness to give a crude product of guanidinium sulfate in a purity of about 85%. This crude product can be readily purified by a known technique such as recrystallization into a high purity product.

As is understood from the above description, guanidinium sulfate is prepared very efficiently and economically from the reaction mixture of urea and an ammonium aqua-ammonosulfate obtained by the reaction under atmospheric pressure by the subsequent processing under relatively mild conditions to give a great industrial advantage.

Following is an illustration of the inventive method by way of an example given in detail.

EXAMPLE

Ammonia and sulfuric acid anhydride were reacted together in the gaseous phase to give a reaction product composed of 73.2% of diammonium imidosulfonate, 14.6% of ammonium sulfamate, 6.9% of ammonium sulfate and 5.3% of an acidic matter calculated as $SO_3$ and a uniform mixture of 85.6 g of the above reaction product and 22.2 g of urea was taken in a tall beaker of 300 ml capacity which was covered with a rubber stopper provided with four gas inlet tubes and one gas outlet tube. Each of the gas inlet tubes extended close to the bottom of the beaker into the reactant mixture.

The lower half of the tall beaker was dipped in an oil bath which was gradually heated to increase the temperature at a rate of 6° to 7° C. per minute while ammonia gas was introduced into the beaker at a rate of 200 ml/minute through each of the gas inlet tubes with discharge through the gas outlet tube. The introduction of ammonia gas was continued for 12 minutes with the temperature of the oil bath kept at 260° C. after the moment when the temperature of the oil bath reached 260° C. and then terminated with the reaction mixture allowed to cool down to room temperature to give 108.47 g of a reaction mixture.

This reaction mixture was composed of 25.99% of guanidine sulfate, 26.14% of ammonium sulfate, 28.35% of diammonium imidosulfonate, 16.48% of ammonium

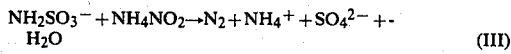

sulfamate, 0.04% of cyanuric acid and 1.78% of an unidentified matter insoluble in hot water.

Into an Erlenmeyer flask of 20 ml capacity were taken 5 g of the above obtained reaction mixture and 2.69 g of water and the flask was sealed air-tightly with a rubber cap and heated with shaking in a water bath thermostatically maintained at 70° C. for 347 minutes to effect the hydrolysis reaction of the reaction mixture. The reason for the so long reaction time was that the reaction was expected to be prolonged due to the absence of sulfuric acid in the reaction mixture at the initial stage of the reaction. The resultant reaction mixture is called primary hydrolysis product hereinafter.

In the next place, the same hydrolysis reaction was repeated as above except that the mixture of 5 g of the reaction mixture and 2.69 g of water was further admixed with the above obtained primary hydrolysis product corresponding to a recycling ratio of 1/1 and the reaction time in this case was 130 minutes at 70° C. The reason for the thus shortened reaction time was that the reaction was expected to be accelerated by the presence of sulfuric acid at the initial stage of the reaction. The composition of the reaction mixture here obtained, which is called secondary hydrolysis product hereinafter, was identical with that of the primary hydrolysis product. Therefore, it was evident that each of the subsequent runs of the hydrolysis reaction could be completed within the reaction time of 130 minutes when a half volume of the secondary hydrolysis product or the hydrolysis product in the preceding run was recycled and added to the new charge of the reactants successively.

A half volume of the secondary hydrolysis product was diluted with water and the insoluble matter, weighing 0.082 g, was removed by filtration to give about 25 ml of a filtrate combined with the washing. Into the filtrate solution were added 2.62 g of calcium hydroxide and the mixture was shaken for 60 minutes followed by further filtration. Into the filtrate solution combined with the washing of the insoluble matter was blown carbon dioxide gas until the pH value of the solution reached 8 followed by filtration to remove the calcium carbonate precipitated in the solution. Evaporation of the filtrate solution to dryness gave 2.164 g of a crude guanidine sulfamate product. The results of the analysis of this product were as follows.

| | |
|---|---|
| Guanidine sulfamate | 84.7% |
| $NH_4^+$ | 3.0% |
| $Ca^{2+}$ | 0.01% |
| $NH_2SO_3^-$ in excess | 3.9% |
| $SO_4^{2-}$ | 6.3% |
| Cyanuric acid | 0.3% |
| $NH(SO_3)_2^{2-}$ | trace |

What is claimed is:

1. In a method for the preparation of guanidine sulfamate by a process wherein urea is reacted with ammonium sulfamate under atmospheric pressure or urea is reacted with ammonium sulfamate or diammonium imidosulfonate or triammonium nitrilosulfonate, or more than one of them, in the presence of ammonia under atmospheric pressure, the improvement whereby guanidium sulfamate is separated from the reaction product by a process which comprises the steps of:
    (a) Forming an aqueous solution of the reaction product,
    (b) Adding hydrolysis product of a preceding run to the solution in an amount effective to promote hydrolysis of the compounds of the reaction products,
    (c) heating the solution to a temperature not exceeding 100° C. to give a hydrolysis product mainly composed of guanidinum ions, ammonium ions, hydrogen ions, sulfamate ions and sulfate ions,
    (d) Admixing the hydrolysis product in which guanidium ions and sulfamate ions are substantially equal, with CaO or $Ca(OH)_2$, and
    (e) Separating the solid components from the liquid containing guanidium sulfamate.

2. The method of claim 1 wherein, where diammonium imidosulfonate is the reactant, the hydrolysis product from the preceding run constitutes ¼ of the mixture to be hydrolyzed.

3. The method claimed in claim 1 wherein the amount of CaO or $Ca(OH)_2$ admixed with the hydrolysis product in the step (d) is from 1.2 to 1.5 times of the equivalent amount of the sulfuric acid and ammonium sulfate contained in the hydrolysis product.

* * * * *